(12) United States Patent
Stepp et al.

(10) Patent No.: US 8,961,672 B2
(45) Date of Patent: Feb. 24, 2015

(54) ORGANOSILICONATE POWDERS, METHOD FOR THE PRODUCTION THEREOF AND USE THEREOF FOR HYDROPHOBIZING MINERAL BUILDING MATERIALS

(75) Inventors: Michael Stepp, Uberackern (AT); Dominik Auer, Muehldorf (DE); Karl-Heinz Felix, Reut (DE); Daniel Schildbach, Altoetting (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 14/119,114

(22) PCT Filed: May 7, 2012

(86) PCT No.: PCT/EP2012/058370
§ 371 (c)(1),
(2), (4) Date: Nov. 20, 2013

(87) PCT Pub. No.: WO2012/159874
PCT Pub. Date: Nov. 29, 2012

(65) Prior Publication Data
US 2014/0069301 A1 Mar. 13, 2014

(30) Foreign Application Priority Data

May 23, 2011 (DE) .......................... 10 2011 076 303
May 24, 2011 (DE) .......................... 10 2011 076 344

(51) Int. Cl.
*C04B 41/49* (2006.01)
*C07F 7/08* (2006.01)
*C07F 7/18* (2006.01)
*C04B 24/42* (2006.01)
*C04B 41/00* (2006.01)
*C04B 41/64* (2006.01)
*C04B 28/02* (2006.01)
*C04B 28/14* (2006.01)

(52) U.S. Cl.
CPC ............. *C04B 24/42* (2013.01); *C04B 41/009* (2013.01); *C04B 41/4927* (2013.01); *C04B 41/64* (2013.01); *C07F 7/08* (2013.01); *C07F 7/18* (2013.01); *C04B 28/02* (2013.01); *C04B 28/14* (2013.01)
USPC .. 106/2; 106/287.1; 106/287.11; 106/287.12; 106/287.13; 106/287.14; 106/287.15; 106/724; 106/727; 106/781; 106/806

(58) Field of Classification Search
CPC .... C04B 14/28; C04B 22/064; C04B 24/383; C04B 24/42; C04B 28/02; C04B 28/14; C04B 41/009; C04B 41/4927; C07F 7/118; C07F 7/08
USPC ............... 106/287.1, 287.11, 287.12, 287.13, 106/287.14, 287.15, 2, 724, 727, 806, 781
See application file for complete search history.

(56) References Cited

U.S. PATENT DOCUMENTS

| | | | |
|---|---|---|---|
| 2,803,561 A | 8/1957 | Kather | |
| 2,898,221 A | 8/1959 | Carlson | |
| 3,914,476 A * | 10/1975 | Nitzsche et al. | 427/337 |
| 3,955,985 A * | 5/1976 | Bosch et al. | 106/2 |
| 3,956,570 A | 5/1976 | Bosch et al. | |
| 4,174,228 A * | 11/1979 | Boberski et al. | 106/686 |
| 4,252,569 A | 2/1981 | Roedel | |
| 4,281,147 A * | 7/1981 | Koerner et al. | 556/459 |
| 4,341,560 A * | 7/1982 | Saito et al. | 524/5 |
| 4,411,701 A * | 10/1983 | Saito et al. | 524/5 |
| 5,178,668 A * | 1/1993 | Traver et al. | 106/2 |
| 6,066,360 A * | 5/2000 | Hirsbrunner et al. | 427/136 |
| 6,368,659 B1 | 4/2002 | Weber et al. | |
| 6,495,649 B2 * | 12/2002 | Harada et al. | 528/39 |
| 6,916,366 B2 * | 7/2005 | Hirsbrunner et al. | 106/287.14 |
| 8,748,645 B2 * | 6/2014 | Schildbach et al. | 556/400 |
| 2007/0084382 A1 * | 4/2007 | Holbek et al. | 106/634 |
| 2010/0212549 A1 * | 8/2010 | Holbek et al. | 106/661 |
| 2014/0121303 A1 * | 5/2014 | Hagen et al. | 524/5 |

FOREIGN PATENT DOCUMENTS

| | | | |
|---|---|---|---|
| DE | 2245927 | 4/1974 | |
| DE | 4336600 C1 * | 10/1994 | ............... C07F 7/18 |
| DE | 10107614 A1 | 8/2002 | |
| EP | 0650968 A1 | 5/1995 | |
| EP | 0992565 A1 | 4/2000 | |
| JP | 49-18853 A * | 2/1974 | ............... C07F 7/18 |
| JP | 2002-322282 A * | 11/2002 | ............ C08G 77/06 |
| RU | 2204571 C1 * | 5/2003 | ............... C07F 7/08 |
| SU | 1032067 A * | 7/1983 | ............ D06M 15/66 |
| WO | WO2012/145659 A1 * | 10/2002 | ............. C04B 41/49 |
| WO | 2010052201 A1 | 5/2010 | |

* cited by examiner

*Primary Examiner* — Anthony J Green
(74) *Attorney, Agent, or Firm* — Brooks Kushman P.C.

(57) ABSTRACT

Solid alkali metal salts of organosilanols and/or their hydrolysis/condensation products are prepared by hydrolysis of organosilanes in water and in the presence of a basic alkali metal salt. The products contain predominately methyl and ethyl organic groups, and $C_4$ or higher hydrocarbon groups as well. The solid salts effectively hydrophobe building materials, while being easily mixed with water.

6 Claims, No Drawings

ORGANOSILICONATE POWDERS, METHOD FOR THE PRODUCTION THEREOF AND USE THEREOF FOR HYDROPHOBIZING MINERAL BUILDING MATERIALS

CROSS-REFERENCE TO RELATED APPLICATIONS

This application is the U.S. National Phase of PCT Appln. No. PCT/EP2012/058370 filed May 7, 2012, which claims priority to German Application Nos. 10 2011 076 303.1, filed May 23, 2011, and German Application No. 10 2011 076 344.9, filed May 24, 2011, the disclosures of which are incorporated in their entirety by reference herein.

BACKGROUND OF THE INVENTION

1. Field of the Invention

The invention relates to organosiliconate powders, to a process for producing them, and to their use, especially for hydrophobizing mineral building materials.

2. Description of the Related Art

Alkali metal organosiliconates have already been used for decades for hydrophobizing—that is, for imparting water repellency to building materials. Generally speaking, these are inorganic building materials which may be silaceous or nonsiliaceous in nature. Aqueous solutions of methylsiliconate, in particular, have a great significance here, particularly the potassium derivative (potassium methylsiliconate) or the sodium derivative (sodium methylsiliconate). On account of their high solubility in water, they can be applied in the form of an aqueous solution to solids, where evaporation of the water is accompanied by the formation of durably water-repellent surfaces which adhere firmly under the influence of carbon dioxide. Since they contain virtually no hydrolytically eliminable organic radicals, curing takes place, advantageously, without release of unwanted volatile organic by-products.

Aqueous solutions of organosiliconates are especially suitable for hydrophobizing weakly acidic to weakly alkaline building materials, more particularly products comprising fired clay, natural stone, cement or gypsum. The hydrophobizing agent may be applied here either by impregnation or mass hydrophobizing. In the case of impregnation, for example, products of fired clay or natural stone are immersed for a certain time into an aqueous dilution of the organosiliconate or are sprayed with a dilution of this kind, the active substance in solution in water penetrating the porous microstructure of the building material by capillary action. After a time of a few minutes or several hours or even a number of days after drying of the building material, depending on the prevailing conditions, a hydrophobic zone is developed which surrounds the building material and drastically reduces its capillary water uptake. In the case of mass hydrophobizing, the aqueous solution of the organosiliconate is mixed, after further dilution where appropriate, with the aqueous slurry of a building material. Measurements of the water uptake of the building material after it has set and dried show a greatly reduced water uptake as compared with the unhydrophobized building material.

For example, U.S. Pat. No. 2,803,561 describes the use of aqueous solutions of organosiliconates and of methyl siliconate powder for hydrophobizing calcium-containing masonry (gypsum, limestone).

The preparation of alkali metal organosiliconates, especially potassium or sodium methylsiliconates, has been often described. In the majority of cases, the focus is on producing aqueous solutions which are ready for application and are stable in storage.

For example, EP 650968 describes a continuous process starting from organotrichlorosilanes and proceeding via the organotrialkoxysilane as an intermediate. Advantageous features of that process are that the alcohol and hydrogen chloride by-products formed are recovered and that the siliconate solution formed is virtually chloride-free.

The advantage of the mass hydrophobizing of gypsum or cement, for example, is that the building material not only is surrounded by a hydrophobic zone but is water-repellent through and through. This is especially important with building materials which have a tendency to be water-soluble, such as gypsum, or if the building material is cut into pieces after the water repellency treatment. This technique is employed, for example, in the production of gypsum plasterboard panels, gypsum wallboarding panels or gypsum fiberboard panels. Plasters and filling compounds or tile adhesives, however, are supplied to the building site as powders, in bags or silos, and are made up with water by stirring on site. For application in gypsum- or cement based plasters, filling compounds, repair filler powders, tile adhesives and similar mineral building materials, therefore, a solid hydrophobizing agent is required that can be added to the ready-to-use dry mixture and which develops its hydrophobizing effect in a short time only on addition of water during application on site, such as on the building site, for example. This is called dry-mix application.

The majority of conventional dry-mix hydrophobizing agents in accordance with the current state of the art are supported systems, which means that a hydrophobizing agent which is in fact in liquid form, such as an active silane and/or siloxane ingredient, for example, is applied to a support material which is more or less chemically inert. The amount of hydrophobizing agent applied in this case is only such as to produce a dry and free-flowable powder. This produces active contents of only 30-50%—it follows from this that the mass of the inactive support material accounts for 50-70% of the total mass. The support material may be inorganic—examples are silicas and silicates—or organic—examples are polyvinyl alcohols, as described in WO 2010052201. By combination with the water used for making up the mix, and by intensive mixing, the liquid hydrophobizing agent develops its effect, while the support material remains in the cured building material as a functionless filling material. The support material may even have adverse effects on the fully cured building material; it is known, for instance, that polyvinyl alcohols tend to increase the hydrophilicity of gypsum building materials, which is counterproductive.

Conventional dry-mix hydrophobizing agents such as salts of fatty acids have a series of disadvantages. With these known products, a problem which occurs is that the high hydrophobicity of the powders and premature migration of the hydrophobizing agent onto the building material which is still to be mixed with water results in a delayed initial miscibility. As a result, in addition to the loss of time, unwanted dust is formed from the building material as a result of the delayed wetting with water. Likewise, conventional dry-mix hydrophobizing agents based on siloxane have a comparatively low active content, because they usually consist of a liquid active siloxane ingredient on a solid support, as described in WO 2010052201, example 1. Apart from its support activity, the support has no importance, and an increase in the active content would lead to sticky dry-mix hydrophobizing agents which would no longer be free-flowable. As a consequence, these hydrophobizing agents are not efficient enough.

The highest active ingredient contents are obtained with unsupported systems, such as the pure siliconate powders described in U.S. Pat. No. 2,803,561, for example. They are suitable in principle as dry-mix additives. For example, DE A 10107614 describes cement-based tile adhesives made water-repellent through addition of 0.1% to 20% of alkali metal siliconate as dry powder. In contrast to the oleates or stearates commonly used, the alkylsilicic acids which form in the building material are said to ensure water vapor permeability and so not to hinder the drying of masonry or screed. Mention is made of alkali metal alkylsiliconates with methyl radicals, ethyl radicals, and also with the various isomeric propyl radicals and butyl radicals. A disadvantage of these additives is that the most effective representatives, with more than two C atoms in the alkyl radical, are obtainable only by way of the expensive intermediate step of a hydrosilylation. In contrast, methylsiliconates, which are available much more cost-effectively from methyltrichlorosilane, a byproduct of the Müller-Rochow process, are not durably water-repellent, especially in strongly basic, cement-based building materials, on account of their solubility in water.

U.S. Pat. No. 2,898,221 as well describes alkali metal alkylsiliconates with methyl, ethyl, propyl, vinyl, or allyl radical as additives for concrete. The siliconates, which can also be used in solid form (column 1/line 43), not only raise the hydrophobicity, but also, in fractions of 0.05%-0.7%, based on the Portland cement employed, give the building material a higher compressive strength, although a retarded setting behavior is likely (column 2/line 2). Mixtures of different siliconates may also be employed (column 1/line 56).

According to DE 2245927, aqueous solutions of alkali metal propylsiliconates, both alone and in blends with other alkyl siliconates, more particularly methyl siliconates, are particularly effective surface water repellency agents for strongly basic building materials which have not yet fully set. They are prepared in two stages by cohydrolysis of propyl-trichlorosilane with other alkyltrichlorosilanes, followed by dissolution in aqueous alkali. Comparative examples with methylsiliconate and ethylsiliconate show their low permanence in the water repellency effect on concrete. From the prior art described it is evident that cost-effective and efficient dry mix additives on a siliconate basis, for universal use both in neutral and in basic building materials, have not so far existed. The methyl siliconates obtainable from the inexpensive methyltrichlorosilane are less well suited to applications in strongly basic environments, such as cement, on account of their ready solubility in water, this poor suitability being evident from a low permanence of the water repellency effect. Conversely, the siliconates that are more effective in cementitious systems, with radicals larger than methyl, have to be prepared via an additional operating step, an expensive hydrosilylation reaction with an olefin as further raw material and, preferably, with the use of expensive platinum catalysts. Mixtures of methyl siliconates and siliconates with larger radicals, besides the extra expense of a dual operating chain from production to warehousing, possess a further great disadvantage: as the size of the organyl radical goes up, there is a decrease in the wettability of the siliconate powder by water, and so even small fractions in the ready-to-apply building material can lead to the abovementioned problems such as retarded mixability and formation of dust on mixing with water.

SUMMARY OF THE INVENTION

The objective is therefore to find efficiently hydrophobicizing siliconates in powder form as dry mix additives both for neutral and for strongly basic building materials, that are based on the inexpensive methyltrichlorosilane to an extent which is as high as possible, and which nevertheless exhibit high water wettability and thus great ease of incorporation by mixing. The object is achieved by the invention, which provides solid salts (P) of organosilanols, of their hydrolysis/condensation products, or of organosilanols together with their hydrolysis/condensation products with alkali-metal cations, wherein the molar ratio of cation to silicon is 0.5 to 3 and of which at least 1 mol % and not more than 99 mol % of the organic radicals present are selected from methyl and ethyl radicals and the other organic radicals contain at least 4 C atoms.

DETAILED DESCRIPTION OF THE PREFERRED EMBODIMENTS

Surprisingly it has been found that alkali metal siliconates which carry not only methyl or ethyl radicals but also larger organyl radicals are readily water-wettable in spite of their low water solubility, exhibit a strong water repellency activity with high permanence, and can be employed universally in mineral building materials.

The solid salts (P) of these alkali metal siliconates effect efficient water repellency and can be used in powder form as dry mix additives both for neutral and for strongly basic building materials. The solid salts (P) are based on the inexpensive methyltrichlorosilane to a high degree, for example, and nevertheless exhibit high water wettability and hence great ease of incorporation into building materials by mixing, and also an excellent activity and permanence even in strongly alkaline building materials.

The invention also provides a process for producing solid salts (P) of organosilanols, of their hydrolysis/condensation products, or of organosilanols together with their hydrolysis/condensation products with alkali metal cations, by subjecting in a first step organosilanes of the general formula 1

$$(R^1)_a Si(Y)_b (-Si(R^2)_{3-c}(Y)_c)_d \qquad (1)$$

or their hydrolysis/condensation products, or the organosilanes of the general formula 1 together with their hydrolysis/condensation products, where $R^1$ and $R^2$ are each a monovalent, Si—C-bonded hydrocarbon radical which is unsubstituted or is substituted by halogen atoms, amino groups, thiol groups or $C_{1-6}$ alkyl- or $C_{1-6}$ alkoxy-substituted silyl groups and has 1 to 30 carbon atoms, in which one or more nonadjacent —$CH_2$— units may be replaced by groups —O—, —S—, or —$NR^3$—, and in which one or more nonadjacent =CH— units may be replaced by groups —N=, $R^3$ is hydrogen or a monovalent hydrocarbon radical having 1 to 8 carbon atoms which is unsubstituted or substituted by halogen atoms or $NH_2$ groups, Y is hydrogen, F, Cl, Br, or $OR^4$, $R^4$ is a monovalent hydrocarbon radical which is unsubstituted or substituted by halogen atoms or silyl groups and has 1 to 10 carbon atoms, in which one or more nonadjacent $CH_2$ units may be replaced by groups —O—, —S—, or —$NR^3$—, and in which one or more nonadjacent =CH— units may be replaced by groups —N=, a denotes the values 1, 2 or 3, and b, c, and d denote the values 0, 1, 2 or 3, with the proviso that $b+c \geq 1$ and $a+b+d=4$, to hydrolysis in the presence of water and basic salt of alkali metal cations, the amount of basic salt being calculated such that per mole of silicon there is 0.5 mol to 3 mol of cations, and, if the organosilanes of the general formula 1 contain radicals selected from F, Cl, and Br, a further mole of basic salt is present per mole of F, Cl, and Br, and at least 1% and not more than 99% of the radicals $R^1$ and $R^2$ are selected from methyl and ethyl radicals and the other radicals $R^1$ and $R^2$ contain at least 4 C atoms, in a second step, removing the liberated compound HY in the form of gas, in a third step, removing water present in the mixture, and in a fourth step, isolating the salt (P) in the form of a solid.

In the case of the solid salts (P) of organosilanols, the organosilanols are preferably the reaction products of the organosilanes of the general formula 1. The alkali metal cations and the molar ratios are preferably the alkali metal cations named in the production process and the molar rations specified therein.

In the salt of the invention the preferred molar ratio of cation to silicon is at least 0.55, preferably at least 0.6, more preferably at least 0.7, most preferably at least 0.8 and not more than 2.8, preferably not more than 2.0, more preferably not more than 1.5, and most preferably not more than 1.1. The cation is preferably selected from sodium and potassium.

The individual steps in the process of the invention need not run separately one after another in terms of time, strictly speaking, but instead, depending on the nature of the substances employed, are designed in such a way that, in order to maximize the space/time yield, they run largely parallel or at least flow seamlessly into one another, but can optionally also proceed in another order.

In place of monomeric compounds of general formula 1 it is also possible to use their hydrolysis/condensation products, which are formed, for example, by partial hydrolysis of the individual or mixed monomeric compounds of the general formula 1 or by alcoholysis of the corresponding chlorosilane precursors with moist alcohol, and optionally in a mixture with the respective monomers.

In the case of the organosilanes of the general formula 1, for a rapid and complete reaction, a certain fraction of unhydrolyzed and/or uncondensed monomers is preferred, and so the mixture as a whole contains preferably at least 60%, more preferably at least 80%, and more particularly at least 90% of all of its silicon-containing constituents in monomeric form. Tolerable oligomer fractions arise when, for example, the alcohol $HOR^4$, removed by distillation in the second step of the process of the invention, already contains certain fractions of water and is used again for preparing the alkoxysilanes. The establishment of a circuit in terms of substances significantly increases the economics of the overall procedure.

It is possible as well to use mixed oligomers of organosilanes of the general formula 1, or mixtures of these mixed oligomeric siloxanes with monomeric silanes of the general formula 1. Any silanol groups, formed by hydrolysis, that are present in the compounds of the general formula 1 or their oligomers are not disruptive.

It is preferably the case that for not more than 10 mol %, more preferably not more than 1 mol %, of the compounds of the general formula 1, Y is hydrogen.

$R^1$ and $R^2$ may be linear, branched, cyclic, aromatic, saturated, or unsaturated. Examples of amino groups in $R^1$ and $R^2$ are radicals —$NR^5R^6$, where $R^5$ and $R^6$ may be hydrogen or a $C_1$-$C_8$-alkyl, cycloalkyl, aryl, arylalkyl or alkylaryl radical, which may be substituted by —OR', where $R^7$ may be $C_1$-$C_8$-alkyl, aryl, arylalkyl or alkylaryl. If $R^5$ and $R^6$ are alkyl radicals, nonadjacent $CH_2$ units therein may be replaced by groups —O—, —S—, or —$NR^3$—. $R^5$ and $R^6$ may also constitute a ring system. $R^5$ is preferably hydrogen or an alkyl radical having 1 to 6 carbon atoms.

$R^1$ and $R^2$ in the general formula 1 are each preferably a monovalent hydrocarbon radical having 1 to 18 carbon atoms which is unsubstituted or substituted by halogen atoms or by amino, alkoxy or silyl groups. Particularly preferred are unsubstituted alkyl radicals, cycloalkyl radicals, alkylaryl radicals, arylalkyl radicals, and phenyl radicals. The hydrocarbon radicals $R^1$ and $R^2$ preferably have 1 to 8 carbon atoms. Particularly preferred are the methyl, ethyl, propyl, 2-propyl(=isopropyl), 3,3,3-trifluoropropyl, vinyl, 1-n-butyl, 2-methylpropyl (=isobutyl), 1-n-pentyl, 1-n-hexyl, 1-n-heptyl, 1-n-octyl, 2,4,4-trimethyl-1-pentyl, 2-ethyl-1-hexyl, 2-methyl-1-pentyl radical, and the radicals included under the collective terms isohexyl and isooctyl, and the phenyl radical, more particularly the methyl, ethyl, propyl, isobutyl, 1-n-hexyl, 1-n-octyl, isohexyl and isooctyl radical.

Further examples of radicals $R^1$ and $R^2$ are as follows: 3-chloropropyl, chloromethyl, 2-(trimethylsilyl)ethyl, 2-(trimethoxysilyl)ethyl, 2-(triethoxysilyl)ethyl, 2-(dimethoxymethylsilyl)ethyl, 2-(diethoxymethylsilyl)ethyl, 2-butyl, tert-butyl, n-pentyl, cyclopentyl, cyclohexyl, n-nonyl, n-decyl, n-undecyl, 10-undecenyl, n-dodecyl, isotridecyl, n-tetradecyl, n-hexadecyl, allyl, benzyl, p-chlorophenyl, o-(phenyl) phenyl, m-(phenyl)phenyl, p-(phenyl)phenyl, 1-naphthyl, 2-naphthyl, 2-phenylethyl, 1-phenylethyl, 3-phenylpropyl, 3-(2-aminoethyl)aminopropyl, 3-aminopropyl, N-morpholinomethyl, N-pyrrolidinomethyl, 3-(N-cyclohexyl)aminopropyl, 1-N-imidazolidinopropyl radical.

Further examples of $R^1$ and $R^2$ are radicals —$(CH_2O)_n$—$R^8$, —$(CH_2CH_2O)_m$—$R^9$, and —$(CH_2CH_2NH)_o$H, where n, m and o denote values from 1 to 10, more particularly 1, 2, or 3, and $R^8$ and $R^9$ have the definitions of $R^5$ and $R^6$.

$R^3$ is preferably hydrogen or an alkyl radical having 1 to 6 carbon atoms which is unsubstituted or substituted by halogen atoms. Examples of $R^3$, more particularly of alkyl radicals, are listed above for $R^1$.

$R^4$ in the general formula 1 may have ethylenically unsaturated double bonds or be saturated. Preference is given to a monovalent alkyl radical having 1 to 4 carbon atoms which is optionally substituted by alkoxy groups having 1 to 3 carbon atoms and may be linear or branched. The radicals in question are preferably linear alkyl radicals, very preferably the methyl and ethyl radicals, and particularly the methyl radical.

Further examples of radicals $R^4$ are as follows: n-propyl, 2-propyl, n-butyl, 2-butyl, 2-methylpropyl, tert-butyl, 2-(methoxy)ethyl, 2-(ethoxy)ethyl radical, 1-propen-2-yl radical.

If d=0, then the fraction of compounds of the general formula 1 for which a=2 or 3, optionally their hydrolysis/condensation products, or their fraction in mixed hydrolysis/condensation products with compounds of the general formula 1 where a=1, is preferably such as to produce solids, and the fraction is preferably 0 to 20 mol %, more preferably 0 to 10 mol %, more particularly 0 mol %, based on the total amount of silane of the general formula 1 and/or its hydrolysis/condensation products.

Preferably, d is the value 0. Preferably in not more than 20 mol %, and more preferably not more than 5 mol % of the compounds of the general formula 1, d has a value of 1, 2 or 3.

Examples of compounds of the general formula 1 where a=1 are as follows:
MeSi(OMe)$_3$, MeSi(OEt)$_3$, MeSi(OMe)$_2$(OEt), MeSi(OMe)(OEt)$_2$, MeSi(OCH$_2$CH$_2$OCH$_3$)$_3$, H$_3$C—CH$_2$—CH$_2$—Si(OMe)$_3$, (H$_3$C)$_2$CH—Si(OMe)$_3$, CH$_3$CH$_2$CH$_2$CH$_2$—Si(OMe)$_3$, (H$_3$C—CH$_2$)CH(CH$_3$)—Si(OMe)$_3$, $(H_3C)_2CHCH_2$—Si(OMe)$_3$, tBu-Si(OMe)$_3$, PhSi(OMe)$_3$, PhSi(OEt)$_3$, $F_3C$—$CH_2$—$CH_2$—Si(OMe)$_3$, $H_2C$=CH—Si(OMe)$_3$, HS—$CH_2CH_2CH_2$—Si(OMe)$_3$, $H_2C$=CH—Si(OEt)$_3$, $H_2C$=CH—Si(OMe)$_3$, Cl—$CH_2CH_2CH_2$—Si(OMe)$_3$, cy-Hexyl-Si(OEt)$_3$, n-hexyl-Si(OMe)$_3$, isohexyl-Si(OMe)$_3$, cy-hexyl-$CH_2$—$CH_2$—Si(OMe)$_3$, $H_2C$=CH—$(CH_2)_9$—Si(OMe)$_3$, $CH_3CH_2CH_2CH_2CH(CH_2CH_3)$—$CH_2$—Si(OMe)$_3$, isooctyl-Si(OMe)$_3$, isooctyl-Si(OEt)$_3$, n-octyl-Si(OMe)$_3$, n-octyl-Si(OEt)$_3$, hexadecyl-Si(OMe)$_3$, Cl—$CH_2$—Si(OMe)$_3$, $H_2N$—$(CH_2)_3$—Si(OEt)$_3$, cyHex-NH—$(CH_2)_3$—Si(OMe)$_3$, $H_2N$—$(CH_2)_2$—NH—$(CH_2)_3$—Si(OMe)$_3$, $O(CH_2CH_2)_2N$—$CH_2$—Si—(OEt)$_3$, PhNH—$CH_2$—Si(OMe)$_3$, hexadecyl-SiH$_3$, MeSi(OEt)$_2$H, PhSi(OEt)$_2$H, PhSi(OMe)$_2$H, MeSi(OEt)H$_2$, propyl-Si(OMe)$_2$H, MeSiH$_3$, MeSi(OEt)(OMe)H, (MeO)$_3$Si—$CH_2CH_2$—Si(OMe)$_3$, (EtO)$_3$Si—$CH_2CH_2$—Si(OEt)$_3$, $Cl_3$Si—$CH_2CH_2$—SiMeCl$_2$, $Cl_3$Si—$CH_2CH_2$—SiCl$_3$, $Cl_3$Si—$(CH_2)_6$—SiCl$_3$, (MeO)$_3$SiSi(OMe)$_2$Me, MeSi(OEt)$_2$Si(OEt)$_3$, MeSiCl$_2$SiCl$_3$, Cl$_3$SiSiCl$_3$, HSiCl$_2$SiCl$_2$H, HSiCl$_2$SiCl$_3$, MeSiCl$_3$, MeSiCl$_2$H, $H_2C$=CH—SiCl$_3$, PhSiCl$_3$, $F_3C$—$CH_2$—$CH_2$—SiCl$_3$, Cl—$CH_2CH_2CH_2$—SiCl$_3$, MeSi(OMe)Cl$_2$, MeSi(OEt)ClH, EtSiBr$_3$, MeSiF$_3$, Cl—$CH_2$—SiCl$_3$, Cl$_2$CH—SiCl$_3$.

Preference is given to MeSi(OMe)$_3$, MeSi(OEt)$_3$, $(H_3C)_2CHCH_2$—Si(OMe)$_3$ and PhSi(OMe)$_3$, n-hexyl-Si(OMe)$_3$, isooctyl-Si(OMe)$_3$, n-octyl-Si(OMe)$_3$, with methyltrimethoxysilane, n-hexyl-Si(OMe)$_3$, isooctyl-Si(OMe)$_3$ and n-octyl-Si(OMe)$_3$, or their pure or mixed hydrolysis/condensation product being particularly preferred.

Examples of compounds of the general formula 1 where a=2 are as follows:
Me$_2$Si(OMe)$_2$, Me$_2$Si(OEt)$_2$, Me$_2$Si (OCH(CH$_3$)$_2$)$_2$, MeSi(OMe)$_2$CH$_2$CH$_2$CH$_3$, Et$_2$Si(OMe)$_2$, Me$_2$Si(OCH$_2$CH$_2$OCH$_3$)$_2$, MeSi(Ome)$_2$Et, $(H_3C)_2CH$—Si(OMe)$_2$Me, Ph-Si(OMe)$_2$Me, t-Bu -Si(OMe)$_2$Me, Ph$_2$Si(OMe)$_2$, PhMeSi(OEt)$_2$, MeEtSi(OMe)$_2$, $F_3C$—$CH_2$—$CH_2$—Si(OMe)$_2$Me, $H_2C$=CH—Si(OMe)$_2$Me, $H_2C$=CH—$CH_2$—Si(OMe)$_2$Me, Cl—$CH_2CH_2CH_2$—Si(OMe)$_2$Me, cy-Hex-Si(OMe)$_2$Me, HS—$CH_2CH_2CH_2$Si(OMe)$_2$Me, cy-Hex-$CH_2$—$CH_2$—Si(OMe)$_2$Me, $H_2C$=CH—$(CH_2)_9$—Si(OMe)$_2$Me, Cl—$CH_2$—SiMe(OMe)$_2$, $H_2N$—$(CH_2)_3$—SiMe(OEt)$_2$, cyHex-NH—$(CH_2)_3$—SiMe(OMe)$_2$, n-hexyl-Si(OMe)$_2$Me, isohexyl-Si(OMe)$_2$Me, isooctyl-Si(OMe)$_2$Me, isooctyl-Si(OEt)$_2$Me, n-octyl-Si(OMe)$_2$Me, n-octyl-Si(OEt)$_2$Me, $H_2N$—$(CH_2)_2$—NH—$(CH_2)_3$—SiMe(OMe)$_2$, $O(CH_2CH_2)_2N$—$CH_2$—SiMe(OMe)$_2$, PhNH—$CH_2$—SiMe(OMe)$_2$, (MeO)$_2$MeSi—$CH_2CH_2$—SiMe(OMe)$_2$, (EtO)$_2$MeSi—$CH_2CH_2$—SiMe(OEt)$_2$, Cl$_2$MeSi—$CH_2CH_2$—SiMeCl$_2$, Cl$_2$MeSi—$CH_2$—SiMeCl$_2$, (MeO)$_2$MeSiSi(OMe)$_2$Me, MeSi(OEt)$_2$SiMe(OEt)$_2$, MeCl$_2$SiSiMeCl$_2$, HClMeSiSiMeClH, Me$_2$SiCl$_2$, Me$_2$SiClH, $H_2C$=CH—SiMeCl$_2$, Ph$_2$SiCl$_2$, MePhSiCl$_2$, $F_3C$—$CH_2$—$CH_2$—SiMeCl$_2$, Cl—$CH_2CH_2CH_2$—SiMeCl$_2$, Me$_2$Si(OMe)Cl, Me$_2$Si(OEt)H, EtSiMeBr$_2$, Me$_2$SiF$_2$, Cl—$CH_2$—SiMeCl$_2$, Cl$_2$CH—SiMeCl$_2$, Me$_2$Si(OEt)H, Me$_2$SiH$_2$, Et$_2$SiH$_2$, EtMeSiH$_2$, Ph$_2$SiH$_2$, Me$_2$Si(OMe)Si(OMe)$_3$, Me$_2$Si(OMe)Si(OMe)Me$_2$, hexadecyl-SiMeH$_2$, Me$_2$Si(OMe)SiMe$_3$, Me$_2$Si(OMe)SiMe(OMe)$_2$.

Preference is given to Me$_2$Si(OMe)$_2$, Me$_2$Si(OEt)$_2$, MeSi(OMe)$_2$CH$_2$CH$_2$CH$_3$, and Ph-Si(OMe)$_2$Me, with Me$_2$Si(OMe)$_2$ and MeSi(OMe)$_2$CH$_2$CH$_2$CH$_3$ being particularly preferred.

Me denotes the methyl radical, Et denotes the ethyl radical, Ph denotes the phenyl radical, t-Bu denotes the 2,2-dimethylpropyl radical, cy-hexyl denotes the cyclohexyl radical, the prefix "iso" (e.g., isohexyl, isooctyl) denotes a branched radical (in the case of the silanes, preferably mixtures with at least one branched radical, isooctyl preferably denotes the 2,4,4-trimethyl-1-pentyl radical), and hexadecyl denotes the n-hexadecyl radical.

It is critical here that at least 1%, preferably at least 10%, more preferably at least 25% and not more than 99%, preferably not more than 90%, more preferably not more than 75% of all the radicals $R^1$ in the compounds of the general formula 1 or the hydrolysis/condensation products thereof are selected from methyl and ethyl radicals.

The basic salts preferably have a $pK_b$ of not more than 12, more preferably not more than 10, and most preferably not more than 5. Basic salts used are compounds which form solvated hydroxide ions in water and comprise alkali metal ions as their cations. Alkali metal salts used are preferably alkali metal hydroxides, such as lithium hydroxide, sodium hydroxide, potassium hydroxide, and cesium hydroxide, more preferably sodium hydroxide and potassium hydroxide. Further examples of alkali metal salts are alkali metal carbonates, such as sodium carbonate and potassium carbonate, and also alkali metal hydrogen carbonates such as sodium hydrogen carbonate, alkali metal formates such as potassium formate, alkali metal silicates (waterglass) such as sodium orthosilicate, disodium metasilicate, disodium disilicate, disodium trisilicate or potassium silicate. It is also possible furthermore to use alkali metal oxides, alkali metal amides or alkali metal alkoxides, preferably those which release the same alcohol as the silanes of the general formula 1 that are used.

Mixtures of different salts, possibly of different alkali metals, can also be used, examples being mixtures of sodium hydroxide and potassium hydroxide. Typical accompanying constituents in technical grades of the basic salts (i.e., at purities between 80% and 99% by weight), such as water or other salt fractions, such as sodium fractions in potassium salts or carbonates in hydroxides, for example, are generally not disruptive, and can be tolerated. Another preferred variant is the use of aqueous preparations of alkali metal siliconates optionally in a mixture with other alkali metal salts, preferably alkali metal hydroxides. This may be advantageous if the aqueous siliconate preparation (solution, suspension, emulsion) is already produced, for example, as a commercial product in large quantities, (e.g., potassium methylsiliconate commercially available from Wacker Chemie AG as SILRES® BS 16), hence necessitating merely one further reaction step in order to produce the solid salts of the invention.

The amount of basic salt is preferably selected such that per mole of silicon there are at least 0.55, preferably at least 0.6, more preferably at least 0.7 and most preferably at least 0.8, and not more than 2.8, preferably not more than 2.0, more preferably not more than 1.5, and, most preferably, not more than 1.1 cations.

In the presence of radicals selected from F, Cl, and Br in the general formula 1, the amount of F, Cl, and Br present is reacted with the stoichiometric amount of base, preferably with alkali metal hydroxide. The resultant neutralization products are impossible or very difficult to separate from the organosiliconate, and therefore preferably remain in the solid salt (P) of the invention, thereby reducing its active ingredient content accordingly. Preferably, therefore, not more than 50 mol %, more preferably not more than 20 mol %, and most preferably not more than 5 mol %, of the compounds of general formula 1 have fluorine, chlorine and/or bromine as Y.

One advantage of the process of the invention is the massive breadth in variation of substances employed that can be tolerated, and the associated relatively low requirements concerning their purity. For this reason, the process is very well suited to deriving value from secondary products and waste products from the overall silane/siloxane system—for example, residues from the direct silane synthesis, partially alkoxylated chlorosilane mixtures, by-products of hydrosilylations, catalyst-containing distillation residues, condensates from CVD operations, and many more. There may also be liquid, solid or gaseous impurities or by-products present, which, provided they cause no disruption, may remain in the product—for example, silica or metal salts, such as iron chloride, iron oxide, aluminum oxide or platinum-containing catalysts—or can easily be removed by the process—such as solvents.

The amount of water used preferably corresponds to the amount required for complete hydrolysis of the radicals Y, optionally reduced by the amount of HY eliminable from the basic salt used and also by the amount of water optionally bound in the alkali metal salt or optionally water formed in condensation processes. Although chemically there is no upper limit to the amount of water, the water fraction will be minimized on economic grounds, since excess water has to be removed again. Owing to the greater ease of metering solutions of the basic salt rather than solids, the desired amount of basic salt is preferably used in solution in the required amount of water. An excess of water, accordingly, will be sensible and acceptable when, for example, the low solubility of the basic salt in water necessitates a greater amount of water for producing a saturated solution than is needed for the hydrolysis in the context of the process of the invention, or when the salt solution is available industrially in a corresponding concentration. An excess of water may also serve to accelerate the hydrolysis reaction and/or to reduce in the salt of the invention any possible residual fraction of unhydrolyzed radicals Y, the hydrolysis of which can lead to delayed release of the corresponding cleavage products (e.g., methanol) on storage of subsequent application as hydrophobizing agent.

With the aim of minimizing emissions when using the solid salts of the invention, for example, as additives in building materials, the aim is preferably for extremely complete hydrolysis of the radicals Y. On account of their high water repellency activity, however, only comparatively low concentrations of the solid salts of the invention need to be used, and so residual amounts of hydrolyzable radicals Y are generally irrelevant from an emissions standpoint, and eliminating them therefore does not justify any increased level of cost and effort. If, in contrast—for particular applications, for example—a particularly high residual level of unhydrolyzed radicals Y is required, it can be brought about by reducing the amount of water employed to the desired degree.

One possibility to reduce the fraction of water is to add the basic salt or basic salt mixture either in pure form as a solid or as a solution in an organic solvent, preferably in the same alcohol which, where appropriate, is liberated during the hydrolysis reaction, and to meter in separately the minimum amount of water that is required. This variant is appropriate when using hydrolyzable alkali metal alkoxides or alkali metal amides as basic salt. However, combinations of different solvents may also be employed, such as mixtures of water and alcohol, for example.

The water which is present in the mixture in the third step and which may be adhering to the salt (P) is introduced as a result of the input materials and/or is formed during the reaction.

The compound HY that is released in the second step may be removed from the reaction mixture in the form of gas or vapor during and/or after the hydrolysis reaction.

Steps 2 and 3 of the process are preferably carried out in the presence of a liquid F which is inert under the reaction conditions, whose boiling point is above that of the compound HY released, and in which the solid siliconate salt obtained has a solubility of not more than 1 wt % at 100° C./1 bar.

Under reaction conditions, the inert liquid F does not intervene in the reaction. Suitable inert liquids F are preferably hydrocarbons, such as alkanes, cycloalkanes, aromatics or alkylaromatics, or mixtures thereof, and also ethers. Preference is given to using alkanes and alkane mixtures, cycloalkanes, and alkylaromatics, more preferably alkane mixtures. Advantageous qualities of alkane mixtures are their favorable price and their ready availability in a variety of defined boiling ranges. Mixtures of different liquids F may also be used. The boiling point of the inert liquid F at 1013 hPa is preferably at least 10° C. and more preferably at least 30° C. above the boiling point of HY.

Examples of liquids F:
n-hexane, cyclohexane, n-heptane, cycloheptane, n-octane, cyclooctane, n-nonane, n-decane, n-dodecane, 2-methylheptane, methylcyclopentane, methylcyclohexane, isoparaffins such as Isopar® C., E, G, H, L, and M from ExxonMobil, benzene, toluene, o-xylene, m-xylene, p-xylene, mesitylene, ethylbenzene, methyl tert-butyl ether, diethyl ether, diphenyl ether, phenyl methyl ether, and di-n-butyl ether.

The proportion of the liquid F in the overall mixture is preferably selected so as to ensure thorough mixing of the resulting suspension and to avoid bonding of the solids particles. This proportion is preferably at least 50% by weight, more preferably at least 100% by weight, and preferably not more than 500% by weight, more particularly not more than 300% by weight, of the expected amount of solid salts (P).

The mixtures of organosilanes of the general formula 1 and/or their hydrolysis/condensation products are preferably introduced initially, and basic salt and water are metered in, preferably in the form of an aqueous solution. Where some or all of Y has the definition F, Cl, Br, it may be more favorable to introduce basic salt and water initially.

To dissolve the reactants or to reduce the viscosity it may be advantageous to add a solvent. For this purpose it is preferred to add the alcohol $HOR^4$ which may be formed in any case in the reaction mixture in the course of the hydrolysis, and/or the inert liquid F. The reaction takes place customarily at a temperature of 0° C. to 150° C. and under the pressure of the surrounding atmosphere. The process may alternatively be carried out under a lower or higher pressure. The heat of reaction released during the hydrolysis may be utilized in order to heat the reaction mixture. The metering time is therefore guided primarily by the thermal performance from the reaction or by the cooling performance of the reactor. The thermal performance is usually not enough to bring mixtures to boiling and to accomplish complete distillative removal of any alcohol released. Preferably, therefore, heating to boiling is carried out during the metering or when metering is at an end, and the alcohol given off is removed by distillation. In order to maximize the space/time yield, the inert liquid F here is preferably metered in at a rate such that the fill level of the reaction vessel remains constant, i.e., such that only the volume of alcohol removed by distillation is replaced by the liquid F. If the liquid F is immiscible with the alcohol that is given off, and has a lower specific weight than the alcohol, this procedure may be easily automated, for example, using a liquid separator which is filled with the inert liquid F before the alcohol distillate is collected. In this case, the amount of liquid F running back into the reaction vessel is exactly the same as that of the alcohol removed by distillation. When the reaction has ended, the alcohol can be withdrawn via the bottom valve of the separator and used again, for example, for preparing the silanes of the general formula 1. In the case of this procedure, the progress of the hydrolysis reaction can be easily monitored by determining the amount of alcohol in the separator, by a volume or weight measurement, for example, and ascertaining the end point. Following distillative removal of the alcohol, the mixture is preferably heated to an extent such that residues of alcohol and water, and also any water formed in the course of condensation processes, are removed in circulation, while the siliconate precipitates as a solid. It is particularly preferred to conduct heating up to the boiling point of the inert liquid F. When a liquid separator is being used, the water collects as the lower phase in the distillate of liquid F, and so the drying procedure can likewise easily be monitored by checking the amount of water separated off.

If the liberated alcohol dissolves in the inert liquid F, it is preferred to carry out distillation without a liquid separator to the boiling point of the higher-boiling liquid F. An option is to carry out fractional distillation via a distillation column with appropriate separation performance, in order to separate alcohol, liquid F, and—optionally—water from one another distillatively. In this case the distillates obtained are typically mixtures of alcohol, liquid F, and—optionally—water, which may either be purified separately or used directly again for preparing the starting compounds. In this procedural variant it is preferred to top up with fresh liquid F during the distillation in an amount such in each case that the reaction mixture remains stirrable.

Where there is no alcohol present or no alcohol released in the reaction mixture, i.e., if Y=hydrogen, F, Cl and/or Br, there are gaseous cleavage products formed, namely hydrogen, HF, HCl, or HBr, and/or there are low-volatility salts formed that remain in the product, meaning that the inert liquid can be separated off immediately after reaction is at an end. The above-described process can be configured in batch operation or continuously.

In a further preferred process variant, one suitable particularly for a continuous regime, a solution of the siliconate salt is prepared first of all, by reaction of the mixtures of organosilanes of the general formula 1 (or their hydrolysis/condensation products, or by reacting the organosilanes of the general formula 1 together with their hydrolysis/condensation products), with basic salt in the presence of water (hydrolysis) (continuously, for example, by the method described in EP 650968, preferably using the amount of water necessary at least for a hydrolysis of the radicals Y, and without full distillative removal of the alcohol possibly liberated). This is done preferably in the absence of the inert liquid F. In the second and third steps, carried out simultaneously, the siliconate salt solution formed is contacted with the inert liquid F under conditions in which the volatile constituents of the solution evaporate and the siliconate salt precipitates as a solid. The siliconate salt solution formed, which as well as the siliconate salt comprises further hydrolysis products such as alcohol or fluoride, chloride or bromide of the basic salt, and optionally excess water, is preferably mixed with the liquid F. When the volatile constituents are removed by distillation, the solid siliconate salt is obtained as a suspension in the liquid F, and can be isolated in the fourth step, for example, by filtration, centrifugation, sedimentation or evaporation of the inert liquid F. In this case it is preferred to introduce the inert liquid F initially and to meter in the solution of the siliconate salt under conditions which ensure immediate evaporation of the volatile constituents. The conditions that are optimum in each particular case may be readily determined by the skilled person by varying the amount of liquid F, temperature, pressure and/or metering rate. If the solution for siliconate salt is contacted in finely divided form—via a nozzle, for example—with the inert liquid F, the evaporation procedure can be accelerated. It is preferred here to introduce the siliconate solution into the liquid F directly below the surface. To accelerate the evaporation process it is also possible for some of the volatile constituents of the metered siliconate salt solution to be drawn off or distilled off in an upstream step, in which case it is advisable on economic grounds, during the hydrolysis, to add only the amount of water necessary for a complete reaction. The siliconate salt particles formed directly during the metered introduction can be removed continuously from the reaction vessel, in the form of a suspension, and supplied to an optionally continuous solids isolation process. The liquid F can be recovered almost completely and used again in the procedure. By this means it is possible to keep sizes of apparatus and quantities of reserve liquid F (hold-up) low, in spite of correspondingly high throughput rates. Another positive effect of this version of the process is the short residence time of the siliconate solution under distillation conditions (preferably above room temperature), allowing even thermally unstable siliconate solutions to be converted completely and without decomposition phenomena into suspensions, which generally enjoy a relatively high thermal stability. Another advantage is that via the temperature of the liquid F during the metering of the siliconate salt solution it is possible to influence the particle size distribution of the siliconate salt particles formed. Generally speaking here, lower temperatures lead to a larger average particle size.

It is an advantage of the process of the invention that solid to pastelike accumulations on the mixing assemblies and the reactor wall detach during this procedure as the degree of drying progresses, and that a fine suspension is formed from which the solid salt (P) of the invention can be isolated by simple solids separation such as filtration, sedimentation or centrifuging. In one preferred version the volatile constituents in the fine suspension are distilled off under the pressure of the surrounding atmosphere or under reduced pressure, and the resultant solid salt is dried. This takes place preferably at temperatures below the decomposition temperature of the suspension and/or of the dried solid, a temperature which requires individual determination (by DSC measurement, for example)—typically, then, at temperatures below 120° C., preferably below 100° C., more preferably below 80° C. This gentle drying prevents overheating and consequent uncontrollable decomposition reactions. The liquid F separated off in the solids isolation procedure can be used for rinsing the plant, in order to flush out final residues of solids, and to increase the yield. The solid, isolated in particular via filtration, sedimentation or centrifuging, can be further dried—preferably to constant weight—by passing optionally heated inert gas through the system, or else in a drying cabinet or heated mixer, optionally under reduced pressure.

The process can be carried out in batch operation, using—for example—a stirred tank or paddle dryer with top-mounted distillation attachment, of the kind customary in multipurpose plants. Owing to the low level of fouling, it is usually not necessary in the course of production campaigns to clean the reactor between the individual batches of solids residues. The process can therefore in principle also be implemented in apparatus without active mixing.

A continuous process in a tube reactor or in a mixing/conveying assembly such as a kneading apparatus or a single-screw or twin-screw extruder or horizontal paddle dryer—preferably with a plurality of chambers for the various process steps—is likewise possible and is advantageous for industrial production.

Whereas steps 2 and 3, in the case of the process variants described above, are carried out in the presence of an inert liquid F, it is also possible in this case for an appropriately heated gas to serve as a heat transfer agent, and with the siliconate salt solution from step 1 being sprayed into said gas, or the heated siliconate solution is pressurized and released through a nozzle (spray drying, flash evaporation). Gas and siliconate solution in this case can be contacted with one another via a two-fluid nozzle. Drying may take place under the pressure of the surrounding atmosphere, or under higher or lower pressure. Serving as gases in this context are air, but preferably—on account of the possible ignition risk, on safety grounds—inert gases such as nitrogen, lean air (with a maximum of 2 vol % of oxygen), argon, or helium. Use may also be made, however, of low-boiling, optionally halogen-substituted hydrocarbons such as methane, ethane, propane, butane, isobutene, propene, ethane, or tetrafluoromethane, trifluoromethane, difluoromethane, and fluoromethane, and also mixtures of different gases. Heat transfer to gas and/or siliconate salt solution may take place here by means of heat transfer media (oils, water, superheated steam), electrical resistance heating, or microwave radiation.

The direct drying of the siliconate salt solution from step 1 with a corresponding dryer is also an option, provided the adhesions that may form during drying (steps 2 and 3) can be detached mechanically (for example, in a paddle dryer, screw dryer, extruder or short-path or thin-film evaporator). The volatile constituents can be removed under the pressure of the surrounding atmosphere or under reduced pressure. This is done preferably at temperatures below the decomposition temperature of the suspension or of the dried solid—this decomposition temperature must be determined individually (by a DSC measurement, for example)—and hence typically at temperatures below 120° C., preferably below 100° C., more preferably below 80° C. This gentle drying prevents instances of overheating and of uncontrollable decomposition reactions triggered as a result. Heating here takes place preferably via electrical resistance heating, heat transfer media (oils, water, superheated steam), or by microwave irradiation.

An advantage of the process of the invention is that the salts (P) are generally obtained in the form of readily manageable bulk material. If particularly uniform or low particle sizes are desired, in order, for example, to enhance the fluidity of the salt (P) of the invention or to ensure a better distribution in the building material, however, it may be advantageous to subject the solid isolating after step 4 to mechanical communition in an additional step (by grinding in an edge runner mill or a ball mill, for example) and, optionally, to classify using screens or pneumatic classification. If a coarser particle size is desired, the solid can be converted into a material of larger particle size (granules, pellets, tablets, dragees) using established methods for example by means of compression molding tools or by addition of a liquid such as water, for example. A free-flow aid or an anticaking agent may also be added, based for example on a solid such as fumed or precipitated silica, clays, chalk, gypsum, cement, talc, lime or organic polymers, or on a liquid such as silicone oils, mineral oils or polyglycols, likewise to influence the free-flowability in the particular manner desired. This can be done, for example, by mixing with a further additive useful in the end application, in a separate step.

The solid salts (P) of the invention are very suitable for use as hydrophobizing agents, more particularly for mineral substrates, building materials and fibers, more particularly natural fibers, such as cellulose and wool, and synthetic fibers. The hydrophobizing of processed fibers, such as textiles, paper, and cardboard, is likewise a ready possibility. Among the mineral building materials, cement-based and gypsum-based hydraulically setting building materials are preferred that contain preferably at least 10% and more particularly at least 20% by weight of gypsum and/or cement.

Among the gypsums, those known as reactive gypsums are preferred: calcium sulfate hemihydrate ($CaSO_4 \ast 0.5\ H_2O$), in the form, for example, of building plaster, stucco plaster, plaster of Paris or insulating plaster, and anhydrites ($CaSO_4$, anhydrite I, II and III), as are obtained from known calcinating processes, starting from natural gypsum or synthetic gypsums. In the calcinating processes, the calcium sulfate dihydrate, calcium sulfate hemihydrate, and anhydrite I, II and III phases may be obtained, in their various forms, in different proportions and mixtures. Other kinds of plaster as well, such as screeding plaster, imitation marble, anhydrite, recycled gypsum and synthetic plasters (obtained in flue gas desulfurization, in the production of phosphoric acid and hydrofluoric acid, or of organic carboxylic acids) are highly suitable. Depending on the target application (e.g., gypsum plasterboard, gypsum wallboarding panel, gypsum fiberboard panel, gypsum plaster, filling compound, screeding plaster, gypsum adhesive, etc.) and region of mining or source, gypsums with different compositions are used as raw materials, although often it is only the term "gypsum-based building material" that is used. The gypsum may comprise additives which facilitate the production of gypsum moldings or gypsum products, or which enhance the qualities of the gypsum moldings and gypsum products. Examples of additives are fillers, such as silicon dioxide, calcium carbonate, and fibers, accelerators, such as calcium sulfate dihydrate, potassium sulfate, or aluminum sulfate, retardants, such as proteins or salts of tartaric acid or of citric acid, plasticizers and water reducers for the gypsum slurry, such as methylcelluloses or other derivatized celluloses, dispersion powders based on polyvinyl alcohol, polyvinyl acetate or derivatives thereof, such as melamine-, naphthalene- or ligno-sulfonates, polyphosphates or polycarboxylates, adhesion promoters for cardboard, such as starches, adhesion promoters for plasters and filling compounds, such as redispersible polymer powders, pH modifier additives, such as hydrated lime, for example, or cements.

Preference is given to the hydrophobizing of building-material powders. The solids of the invention are used more particularly as dry-mix hydrophobizing agents.

The salts of the invention are initially water-wettable (hydrophilic) and result in a building-material powder whose mixing qualities are very good and unimpaired. The powders then rapidly develop hydrophobicity over time, which is required for setting by the building material, such as a gypsum or cement plaster, a gypsum filling compound, or a gypsum-based or cement-based adhesive, for example, and they therefore exhibit an excellent balance between hydrophilicity and hydrophobicity. In their mechanism of action they do not involve any volatile organic compounds (VOCs). As a result of this and of the fact that they contain no deliberately added support materials, they are among the most efficient dry-mix hydrophobizing agents available.

The pH of the building material in question is unimportant for the hydrophobizing effect. Building material mixtures with a neutral pH of 7 can be used, as can building material mixtures with an acidic pH from 3 to 7, and building material mixtures with an alkaline pH from 7 to 13.

The invention likewise relates to building materials in powder form, comprising the solid salts (P).

The salts (P) are not only suitable as dry-mix hydrophobizing additives; they are likewise suitable for hydrophobizing other, more particularly gypsum-based, building materials from industrial manufacture wherein liquid hydrophobizing agents have been used to date. These include, very particularly, gypsum fiberboard panels, in which organic or inorganic fibers are added to the gypsum powder or gypsum slurry for mechanical reinforcement, and gypsum blocks or wallboarding panels, which are bonded by means of plaster bonding mortars to form solid walls in dry construction, in a manner similar to bricks.

The solid salts (P) of the invention are suitable for hydrophobizing gypsum plasterboard. The restriction arising from the relatively low active ingredient content of commercial siliconate solutions as compared, for example, with silicone fluids based on polymethylhydrogensiloxane (e.g., SILRES® BS 94 from Wacker Chemie AG), which have an active ingredient content of around 100%, can be eliminated, especially for the production of gypsum plasterboard, but also for the production of gypsum fiberboard or gypsum wallboarding panels, by using the solid salts (P). For production-associated reasons, 40-60% of commercial siliconate solutions consist of water, which is not the case with the solid salts (P). They consist preferably (i.e., in the case of $Y \neq F$, Cl, Br) completely of active ingredient, and do not contain any water. Nevertheless, in contrast to the customary organic hydrophobizing powders, they have no tendency to undergo dust explosion, which is a further key advantage for safe handling, in connection, for example, with dry-mix production in air. In order to attenuate still further the increase in the pH after addition of the alkali metal methylsiliconate powder in applications that are even more pH-sensitive, and also in the production of gypsum plasterboard, the possibility exists of admixing the solid salts (P) with acidic, pH reducing or buffering additives in solid form, which become active only when water is added in the application. In the case of liquid alkali metal methylsiliconate solutions, this approach is not conceivable, since in aqueous solution there would be a spontaneous neutralization reaction even before the application, and the alkali metal methylsiliconate would be destabilized and deactivated. Acidic additives of this kind may be all substances which provide a buffering or acidically reacting effect in the presence of water, and which can be isolated in solid form or are encapsulated in hydrolyzable or water-soluble coating substances such as polyvinyl alcohol, gelatin or polysaccharides (e.g., cyclodextrins), examples of such substances being hydrogensulfates, sulfuric esters, phosphates, hydrogenphosphates, dihydrogen-phosphates, phosphoric esters and phosphorous esters, iron salts such as iron chloride, aluminum salts such as aluminum sulfate or aluminum nitrate, acidic clay earths, zeolites, silica gels, ion exchangers, long-chain monobasic or polybasic carboxylic acids and also their alkyl or silyl esters or their anhydrides, ammonium salts or phosphonium salts, acidically reacting organic compounds such as vitamin C (ascorbic acid), phenols, alginic acid or sulfonic acids and esters thereof, amidosulfonic acids, taurine, aminocarboxylic acids such as glycine, glutamic acid, or cysteine, phosphonic acids and their esters, aminophosphonic acids, sulfinic acids and their esters, polyacrylic and polymethacrylic acids, lactones, or sultones.

The salts (P) may also be used in combination with other common hydrophobizing additives. For example, they reinforce the hydrophobizing effect of polymethylhydrogensiloxane-based silicone fluids (e.g., SILRES® BS 94 from Wacker Chemie AG) in conveyor-line gypsum.

It is likewise possible to provide plaster of Paris powders with water repellency using the salts (P), in order to provide statues, figures, ornaments, specialty components, impression moldings, and other plaster-based specialist fabrications, in the domestic or other spheres, with resistance to any influence of water.

The salts (P) are likewise suitable for hydrophobizing building materials comprising other hydraulically setting binders, such as cements (Portland, aluminate, blast furnace, magnesia, or phosphate cement, cements with pozzolanic additives, such as fly ash, trass, clay dust, metakaolin, diatomaceous earth or geopolymers, for example), waterglass, or lime. Accordingly the salts of the invention may find application in systems including masonry and adhesive mortars, base renders and decorative renders, tile adhesives, jointing mortars, adhesive mortars and reinforcing mortars for TICS systems, powder paints, cementitious sealing slurries, filling compounds, self-leveling flooring compounds and screeds, and also patching and repair mortars. Furthermore, they can be added to mixtures for producing ready-made concrete components and concrete products, such as architectural facing elements, trafficway borders, fence elements, paving slabs, cement-bound synthetic stone elements, curb stones, table tops, cement fiber slabs, roofing shingles, and concrete roofing stones, concrete troughs or statues, in order to make them water-repellent and hence resistant, for example, to the penetration of pollutants or to freeze/thaw cycles.

Presently in use for the water-repelling impregnation of neutral to slightly alkaline building materials, especially products made of fired clay or natural stone, are dilute solutions of alkali metal alkylsiliconates. Here, a highly diluted aqueous solution is produced from a water-containing concentrate (e.g., SILRES® BS 16 from Wacker Chemie AG), and is diluted with water in a production works for application at the works, or by a formulator for treatment of architectural facings, for production of primers, or for do-it-yourself application. The water-soluble salts among the salts (P) offer the advantage here that instead of the water-containing concentrate it is possible to supply the end user with a powder in 100 percent form, which can then likewise be adjusted, by dissolution in water, to the desired degree of dilution of the solution. In this way it is possible to achieve marked reductions in transport and stockholding costs.

This advantage is likewise manifested for the application of alkali metal alkylsiliconates in borehole injection for establishing dryer conditions in masonry, where the injection of hydrophobizing agents with and without pressure into existing masonry produces horizontal barriers against rising damp. Alkali metal alkylsiliconates are likewise used as additives in silicone resin paints. They have a hydrophobizing effect, increase the abrasion resistance and can be used at the same time for setting the pH. Here as well, aqueous dilutions of the alkali metal alkylsiliconates are employed, which can likewise be produced from water-soluble, highly concentrated salts (P). Here again, by removing water from the equation in the concentrate, significant reductions can be achieved in transport and stockholding costs. The alkali metal alkylsiliconates can likewise be added as solid to the paint formulation.

In addition to the applications already described, the salts (P) may be used, for example, for hydrophobizing properties in the following applications: hydrophobizing of urea-formaldehyde resins; primers based on styrene acrylates; production of acrylic paints; liquids for generating an insulating layer of condensed silicate/siliconate for semiconductors; hydrophobizing of particles (e.g., peroxides, percarbonates, color pigments, silicates and phyllosilicates, fertilizer mixtures); stabilization of celluloses or starches against moisture; in combination with phosphates for improving the moisture, fungus, and fire resistance of wood impregnated with them; additization of borehole rinsing fluids (e.g., alongside graphite) for reducing the loss of drilling fluid in boreholes in leached-out sand (the hydrophobic coating of particles enhances the cleaning of boreholes by preventing the rinsing fluid adhering to the particles); hydrophobizing of fire-resistant foams, panels or fire-extinguishing powders; antigraffiti coatings; additives for injectable mortars and cements; absorbers for acids and/or aqueous biological or organic media; in combination with alkali metal silicates for soil consolidation and soil hydrophobizing, as described in EP 992 565, for example; hydrophobizing additive for landfill wastes for preventing environmentally harmful leaching/extracts; acid-neutralizing and optionally reinforcing filler for elastomers; additives in combination with SiH compounds or aluminum powders for gypsum-based or cement-based foams (e.g., aerated concrete); instant mix for hydrophobic/antimicrobial treatment of textiles, plant seeds, cellulosic materials, wood, stones in combination with biocides; additive for reinforcing and hydrophobizing asphalt; catalysts based on metalasiloxanes by reaction with metal salts such as, for example, chlorides of aluminum, titanium, zinc, tungsten, lanthanum, lead, cadmium, antimony, copper, nickel, rhodium, silver, zirconium, rubidium, manganese, chromium, cobalt, vanadium, molybdenum, iron, tin, platinum, and palladium; bases which become active only on contact with water and at the same time have neutralizing and hydrophobizing effects; adjuvants to laundry detergent powders or dishwasher detergents; additive for color pigments; addition to coatings to counter scale deposits; dry hydrophobizing of all possible solids (such as fertilizers, attractants, herbicides, pesticides, pigments, hygroscopic salts, glass fibers, mineral wool, glass beads, natural stones, sand, chalk, slaked lime or quick lime, paper, fibers see above, biocides, concrete powders, perlite, expanded clay, expanded glass, metal powders, wood flour, wood pellets, chips, ceramic powders, terracotta powders, clay, inorganic fillers); free-flow aids; heterogeneous alkaline catalyst for raising the reactivity of organosilicon compounds in, for example, equilibration reactions; stripping additive for removing old coatings, additive for wood fiberboard panels (e.g., MDF panels).

In all of the abovementioned applications, the salts (P) may also be added to an already water-containing mixture of the substrate to be hydrophobized, in solid form or optionally in dissolved form. This procedure is appropriate for example if a building material is to be blended with the salt (P) only on the building site. The extent of the desired effect can then be adjusted easily via the amount of (P) added.

All of the above symbols in the above formulae have their definitions in each case independently of one another. In all formulae the silicon atom is tetravalent.

In the inventive and comparative examples below, unless indicated otherwise in each case, all quantity figures and percentage figures are given by weight, and all reactions are carried out under a pressure of 0.10 MPa (abs.).

PREPARATION EXAMPLE 1

Siliconate from methyltrimethoxysilane/isobutyltrimethoxysilane/KOH (0.5:0.5:1)

A 500 ml 5-neck round-bottom flask rendered inert with nitrogen and equipped with paddle stirrer, dropping funnel, thermometer, and water separator with reflux condenser is charged—in an oil bath at 40° C.—with 28 g (0.157 mol) of isobutyltrimethoxysilane (=2-methyl-1-propyltrimethoxysilane, available commercially from abcr GmbH & Co. KG), 21.8 g (0.157 mol) of methyltrimethoxysilane (available commercially from Wacker Chemie AG), and 66 g of Isopar E (isoparaffinic hydrocarbon mixture with a boiling range of 113-143° C., available commercially from ExxonMobil). The water separator is filled to the brim with Isopar E. While stirring at 350 rpm, a solution of 20.7 g (0.314 mol) of potassium hydroxide (85% strength, available commercially from AppliChem) in 16.7 g of demineralized water is metered in over 10 minutes. During this addition, the reaction mixture warms up to 48° C. By subsequent heating it is bought to boiling temperature. The distillate separates out as the lower phase in the water separator. Up to a boiling temperature of 118° C., 34.3 g of clear colorless distillate are collected, which according to analysis by gas chromatography contains 87.4% methanol, 8.6% water, and 3% Isopar E. The hydrolysis of the methoxy radicals, accordingly, is quantitative. During the distillation, a pasty white solid separates out in the reaction mixture. The volatile constituents are removed by distillation at 70° C./4 hPa. The residue left is a white, coarse powder whose solids content is 97.5% (determined using the HR73 Halogen Moisture Analyzer solids content balance from Mettler Toledo at 160° C.).

NONINVENTIVE COMPARATIVE EXAMPLE

Mixture of methylsiliconate and isobutylsiliconate

C1a) Siliconate from isobutyltrimethoxysilane/KOH (1:1)

A 1000 ml 5-neck round-bottom flask rendered inert with nitrogen and equipped with paddle stirrer, dropping funnel, thermometer, and water separator with reflux condenser is charged—in an oil bath at 40° C.—with 117 g (0.636 mol) of isobutyltrimethoxysilane (=2-methyl-1-propyltrimethoxysilane, available commercially from abcr GmbH & Co. KG) and 155.6 g of Isopar E (isoparaffinic hydrocarbon mixture with a boiling range of 113-143° C., available commercially from ExxonMobil). The water separator is filled to the brim with Isopar E. While stirring at 350 rpm, a solution of 42 g (0.636 mol) of potassium hydroxide (85% strength, available commercially from AppliChem) in 32.1 g of demineralized water is metered in over 10 minutes. During this addition, the reaction mixture warms up to 48° C. By subsequent heating it is bought to boiling temperature. The distillate separates out as the lower phase in the water separator. Up to a boiling temperature of 118° C., 73.5 g of clear colorless distillate are collected, which according to analysis by gas chromatography contains 87.1% methanol, 8% water, and 3.6% Isopar E. The hydrolysis of the methoxy radicals, accordingly, is quantitative. During the distillation, a pasty white solid separates out in the reaction mixture. The volatile constituents are removed by distillation at 70° C./4 hPa. The residue left is 94 g of a white, fine powder whose solids content is 99% (determined using the HR73 Halogen Moisture Analyzer solids content balance from Mettler Toledo at 160° C.)

C1b) Siliconate from methyltrimethoxysilane/KOH (1:1)

A 500 ml 5-neck round-bottom flask rendered inert with nitrogen and equipped with paddle stirrer, dropping funnel, thermometer, and water separator with reflux condenser is charged with 60 g (0.44 mol) of methyltrimethoxysilane (available commercially from Wacker Chemie AG), and 100 g of 25% strength potassium hydroxide solution (0.44 mol KOH) are metered in over 10 minutes at 68° C. Following distillative removal of the methanol that is liberated, a clear, colorless solution is obtained. It is admixed with 77.2 g of Isopar E (isoparaffinic hydrocarbon mixture with a boiling range of 113-143° C., available commercially from Exxon- Mobil) and heated to reflux. The distillate separates out in the water separator as the lower phase, and at the same time a finely particulate suspension is formed in the reaction flask. As soon as water no longer separates out, the residue is evaporated to dryness at 100° C./4 hPa. 46.3 g of a white, fine powder are isolated, with a solids content of 99.8% (determined using the HR73 Halogen Moisture Analyzer solids content balance from Mettler Toledo at 160° C.).

C1c) Siliconate from methyltrimethoxysilane/KOH (1:0.85)

A 500 ml 5-neck round-bottom flask rendered with nitrogen and equipped with paddle stirrer, dropping funnel, thermometer, and water separator with reflux condenser, is charged with 75 g (0.55 mol) of methyltrimethoxysilane (available commercially from Wacker Chemie AG) and with 65 g of Isopar E (isoparaffinic hydrocarbon mixture with a boiling rate of 113-143° C., available commercially from ExxonMobile). The water separator is filled with the brim with Isopar E. With stirring at 350 rpm, a solution of 30.9 g (0.47 mol) of potassium hydroxide (85% purity, available commercially from AppliChem) in 19.8 g of demineralized water is metered in over 10 minutes. During this addition, the reaction mixture warms up to 69° C. It is bought to boiling temperature by subsequent heating and the stirrer speed is reduced to 50 rpm. The distillate separates out at the lower phase in the water separator. Up to a boiling temperature of 121° C., 64.9 g of clear, colorless distillate are collected, which according to analysis by gas chromatography contains 83.3% methanol, 14.6% water, and 1.7% Isopar E. The hydrolysis of the methoxy radicals in the methyltrimethoxysilane, accordingly, is quantitative. During the distillation, a pasty white solids separates out in the reaction mixture, and increasingly breaks down into fine particles and forms a suspension. The suspension is filtered over a Beco KD3 filter plate in a suction filter, and nitrogen is passed through to constant weight. This gives 61.1 g of fine, white, free-flowing powder, with a solids content of 100% (determined using the HR73 Halogen Moisture Analyzer solids content balance from Mettler Toledo at 160° C.)

PREPARATION EXAMPLE 2

Siliconate from methyltrimethoxysilane/isohexyltriethoxysilane/KOH (0.5:0.5:1)

A 500 ml 5-neck round-bottom flask rendered inert with nitrogen and equipped with paddle stirrer, dropping funnel, thermometer, and water separator with reflux condenser is charged with 45 g (0.18 mol) of isohexyltriethoxysilane (=4-methyl-1-pentyltriethoxy-silane laboratory product, prepared by reaction of isohexyltrichlorosilane with ethanol; isohexyltrichlorosilane is available through hydrosilylation reaction from 4-methyl-1-pentene and trichlorosilane), 25 g (0.18 mol) of methyltrimethoxysilane (available commercially from Wacker Chemie AG), and 94.3 g of Isopar E (isoparaffinic hydrocarbon mixture with a boiling range of 113-143° C., available commercially from ExxonMobil). With stirring at 300 rpm, 43 g of 47% strength potassium hydroxide solution (0.36 mol KOH) are metered in over 10 minutes, during which the solution is heated to boiling temperature. The distillate separates out as the lower phase in the water separator. Up to a boiling temperature of 118° C., 57.2 g of clear colorless distillate are collected, which according to analysis by gas chromatography contains 43.3% ethanol, 31.8% methanol, 23.1% water, and 1.8% Isopar E. The hydrolysis of the ethoxy and methoxy radicals, accordingly, is quantitative. During the distillation, the reaction mixture undergoes transformation into a suspension. The volatile constituents are removed by distillation at 95° C./4 hPa. The residue left is a white, fine powder whose solids content is 97.1% (determined using the HR73 Halogen Moisture Analyzer solids content balance from Mettler Toledo at 160° C.)

NONINVENTIVE COMPARATIVE EXAMPLE C2

Siliconate from isohexyltrimethoxysilane/KOH (1:1)

A 500 ml 5-neck round-bottom flask rendered inert with nitrogen and equipped with paddle stirrer, dropping funnel, thermometer, and water separator with reflux condenser is charged with 27 g (0.13 mol) of isohexyltrimethoxysilane (=4-methyl-1-pentyltrimethoxysilane laboratory product, prepared by reaction of isohexyltrichlorosilane with methanol; isohexyltrichlorosilane is available through hydrosilylation reaction from 4-methyl-1-pentene and trichlorosilane), and 25 g of Isopar E (isoparaffinic hydrocarbon mixture with a boiling range of 113-143° C., available commercially from ExxonMobil). With stirring at 300 rpm, 14.7 g of 50% strength potassium hydroxide solution (0.13 mol KOH) are metered in over 10 minutes, during which the solution is heated to reflux. The distillate separates out as the lower phase in the water separator. Up to a boiling temperature of 118° C., 16 g of clear colorless distillate are collected, which according to analysis by gas chromatography contains 77.1% methanol, 22.1% water, and 0.7% Isopar E. The hydrolysis of the methoxy radicals, accordingly, is quantitative. During the distillation, the reaction mixture undergoes transformation into a suspension. The volatile constituents are removed by distillation at 70° C./4 hPa. The residue left is a white, floury powder whose solids content is 99.4% (determined using the HR73 Halogen Moisture Analyzer solids content balance from Mettler Toledo at 160° C.)

PREPARATION EXAMPLE 3

Siliconate from methyltrimethoxysilane/isooctyltrimethoxysilane/KOH (0.75:0.25:0.85)

A 500 ml 5-neck round-bottom flask rendered inert with nitrogen and equipped with paddle stirrer, dropping funnel, thermometer, and water separator with reflux condenser is charged with 20 g (0.085 mol) of isooctyltrimethoxysilane (=2,4,4-trimethyl-1-pentyltrimethoxysilane, available commercially from Wacker Chemie AG as SILRES® BS 1316), 35 g (0.25 mol) of methyltrimethoxysilane (available commercially from Wacker Chemie AG), and 41 g of Isopar E (isoparaffinic hydrocarbon mixture with a boiling range of 113-143° C., available commercially from ExxonMobil). With stirring at 300 rpm, 32.1 g of 50% strength potassium hydroxide solution (0.286 mol KOH) are metered in over 10 minutes. This is followed by heating to reflux, with the water separator filled to the brim with Isopar E. The distillate separates out as the lower phase in the water separator. Up to a boiling temperature of 118° C., 41.4 g of clear colorless distillate are collected, which according to analysis by gas chromatography contains 80.4% methanol and 18.4% water. The hydrolysis of the methoxy radicals, accordingly, is quantitative. During the distillation, the reaction mixture undergoes transformation into a suspension. The volatile constituents are removed by distillation at 100° C./4 hPa. The residue left is 46.3 g of a white, coarse powder whose solids content is 99.9% (determined using the HR73 Halogen Moisture Analyzer solids content balance from Mettler Toledo at 160° C.)

NONINVENTIVE COMPARATIVE EXAMPLE C3

Mixture of methylsiliconate and isooctylsiliconate

C3a) Siliconate from isooctyltrimethoxysilane/KOH (1:0.85)

A 500 ml 5-neck round-bottom flask rendered inert with nitrogen and equipped with paddle stirrer, dropping funnel, thermometer, and water separator with reflux condenser is charged with 60 g (0.25 mol) of isooctyltrimethoxysilane (=2,4,4-trimethyl-1-pentyltrimethoxysilane, available commercially from Wacker Chemie AG as SILRES® BS 1316), and 55.7 g of Isopar E (isoparaffinic hydrocarbon mixture with a boiling range of 113-143° C., available commercially from ExxonMobil). With stirring 27.8 g of 43% strength potassium hydroxide solution (0.21 mol KOH) are metered in over 6 minutes. This is followed by heating to reflux, with the water separator filled to the brim with Isopar E. The distillate separates out as the lower phase in the water separator. Up to a boiling temperature of 119° C., 33.5 g of clear colorless distillate are collected, which according to analysis by gas chromatography contains 64.6% methanol and 34.7% water. Therefore 90% of the methoxy radicals are hydrolyzed. During the distillation, the reaction mixture undergoes transformation into a suspension. The volatile constituents are removed by distillation at 100° C./4 hPa. The residue left is 53.3 g of a white, fine powder whose solids content is 99.8% (determined using the HR73 Halogen Moisture Analyzer solids content balance from Mettler Toledo at 160° C.)

C3b) Siliconate from methyltrimethoxysilane/KOH (1:0.85)

A 1000 ml 4-neck laboratory reactor rendered inert using nitrogen and equipped with paddle stirrer, dropping funnel, thermometer, and water separator with reflux condenser is charged with 350 g (2.525 mol) of methyltrimethoxysilane (available commercially from Wacker Chemie AG) in solution in 222.8 g of Isopar E (isoparaffinic hydrocarbon mixture with a boiling range of 113-143° C., available commercially from ExxonMobil). Over the course of 12 minutes, 233.6 g of 50% strength potassium hydroxide solution (0.214 mol KOH) are metered in at 40° C., during which the reaction mixture heats up to reflux (70° C.). It is held at reflux temperature by subsequent heating. The distillate separates out in the water separator as the lower phase, and is continuously taken off and replaced by Isopar E; at the same time, a fine suspension is formed in the reaction flask. Up to a boiling temperature of 118° C., 294.1 g of clear, colorless distillate are collected, which according to analysis by gas chromatography contains 82.4% methanol, 15.7% water, and 1.7% Isopar E. The hydrolysis of the methoxy radicals, accordingly, is quantitative. The suspension is filtered over a Seitz K250 filter plate in a suction filter, and nitrogen is passed through to constant weight. This gives 278.5 g of a very fine, white, free-flowing powder, with a solids content of 99.8% (determined using the HR73 Halogen Moisture Analyzer solids content balance from Mettler Toledo at 160° C.)

PREPARATION EXAMPLE 4

Siliconate from methyltrimethoxysilane/isobutyltrimethoxysilane/KOH (0.3:0.7:1)

A 500 ml 5-neck round-bottom flask rendered inert with nitrogen and equipped with paddle stirrer, dropping funnel, thermometer, and water separator with reflux condenser is charged—in an oil bath at 40° C.—with 77.4 g (0.42 mol) of isobutyltrimethoxysilane (=2-methyl-1-propyltrimethoxysilane, available commercially from abcr GmbH & Co. KG), 25 g (0.18 mol) of methyltrimethoxysilane (available commercially from Wacker Chemie AG), and 78.3 g of Isopar (isoparaffinic hydrocarbon mixture with a boiling range of 113-143° C., available commercially from ExxonMobil). The water separator is filled to the brim with Isopar E. While stirring at 300 rpm, 67.5 g of 50% strength potassium hydroxide solution (0.6 mol KOH) are metered in over 10 minutes. During this addition, the reaction mixture warms up to 63° C. By subsequent heating it is brought to boiling temperature. The distillate separates out as the lower phase in the water separator. It is removed from time to time and replaced each time by Isopar E. Up to a boiling temperature of 118° C., 74 g of clear colorless distillate are collected, which according to analysis by gas chromatography contains 75:5% methanol, 23.6% water, and 0.6% Isopar E. Thus 97% of the methoxy radicals are hydrolyzed. During the distillation, a suspension is formed in the reaction mixture. The volatile constituents are removed by distillation at 70° C./4 hPa. The residue left is 96.5 g of a white, coarse powder whose solids content is 99.4% (determined using the HR73 Halogen Moisture Analyzer solids content balance from Mettler Toledo at 160° C.)

PREPARATION EXAMPLE 5

Siliconate from methyltrimethoxysilane/isobutyltrimethoxysilane/KOH (0.75:0.25:0.85)

A 500 ml 5-neck round-bottom flask rendered inert with nitrogen and equipped with paddle stirrer, dropping funnel, thermometer, and water separator with reflux condenser is charged—in an oil bath at 40° C.—with 15.2 g (0.082 mol) of isobutyltrimethoxysilane (=2-methyl-1-propyltrimethoxysilane, available commercially from abcr GmbH & Co. KG), 34.4 g (0.247 mol) of methyltrimethoxysilane (available commercially from Wacker Chemie AG), and 65.9 g of Isopar (isoparaffinic hydrocarbon mixture with a boiling range of 113-143° C., available commercially from ExxonMobil). The water separator is filled to the brim with Isopar E. While stirring at 250 rpm, a solution of 18.5 g (0.28 mol) of potassium hydroxide (85% form, available commercially from AppliChem) in 11.9 g of demineralized water is metered in over 10 minutes. During this addition, the reaction mixture warms up to 46° C. By subsequent heating it is brought to boiling temperature. The distillate separates out as the lower phase in the water separator. It is removed from time to time and replaced each time by Isopar E. Up to a boiling temperature of 118° C., 37.1 g of clear colorless distillate are collected, which according to analysis by gas chromatography contains 85.6% methanol, 10.8% water, and 2.8% Isopar E. The hydrolysis of the methoxy radicals, accordingly, is quantitative. During the distillation, a suspension is formed in the reaction mixture. The suspension is filtered over a Beco KD3 filter plate in a suction filter, and the filter cake is subsequently dried at 110° C./4 hPa. This gives 37.8 g of fine, white powder, with a solids content of 99.8% (determined using the HR73 Halogen Moisture Analyzer solids content balance from Mettler Toledo at 160° C.)

PREPARATION EXAMPLE 6

Siliconate from methyltrimethoxysilane/iosoctyltrimethoxysilane/KOH (0.8:0.2:0.85)

A 500 ml 5-neck round-bottom flask rendered inert with nitrogen and equipped with paddle stirrer, dropping funnel, thermometer, and water separator with reflux condenser is charged with 25 g of methanol and heated to reflux. Then in parallel a mixture of 30 g (0.125 mol) of isoocyltrimethoxysilane (=2,4,4-trimethyl-1-pentyltrimethoxysilane, available commercially from Wacker Chemie AG as SILRES® BS 1316) and 69.5 g (0.5 mol) of methyltrimethoxysilane (available commercially from Wacker Chemie AG) and 72.7 g of 40% strength potassium hydroxide solution (0.53 mol KOH) is metered in over 30 minutes. The batch is heated at reflux for half an hour thereafter, and the amount of methanol in the initial charge (=25 g) is removed by distillation. The colorless, clear reaction mixture is transferred to a dropping funnel and introduced dropwise into 81 g of boiling Iospar E (isoparaffinic hydrocarbon mixture with a boiling range of 113-143° C., available commercially from ExxonMobil). The hydrolysate solution is metered at a rate such that the temperature does not fall below 100° C. (approximately 88 g/h). The instantaneous evaporation of the volatile solution constituents, methanol and water, leads to instantaneous formation of a readily stirrable, white suspension of siliconate salt in Isopar E. The distillate separates out as the lower phase in the water separator. The suspension is subsequently evaporated to dryness at 100° C. in an oil bath. The residue left is 81.7 g of a white, fine powder with a solids content of 92% (determined using the HR73 Halogen Moisture Analyzer solids content balance from Mettler Toledo at 160° C.).

Use EXAMPLES WITH CEMENT-BASED DRY MORTARS

Use Examples

Water Repellency Treatment of a Dry Mortar with Inventive Alkali Siliconate Powders and Comparison with Noninventive Alkali Siliconate Mixtures A single-coat plaster with the following composition was used:

| | |
|---|---|
| 15.15% | White cement CEMI 42.5 R-DW |
| 3.03% | Walhalla fine lime hydrate |
| 20.20% | Calcilit 0.1-0.5 mm (CaCO$_3$) |
| 12.48% | Calcilit 100 K (now KA 40) |
| 0.05% | Tylose MH 15002 P 6 |
| 0.10% | Amylotex Plus |
| 27.27% | Ulmer Weiss |
| 20.20% | Calcilit 0.5-1.0 mm |

In order to obtain statistically robust results, at least two test specimens with identical levels of added water repellency agent are always produced.

Procedure:

The prescribed amounts of dry mortar are mixed with the amount of the powdered water repellency agent under test, using the IKA laboratory stirrer (mixing time: at least 20 seconds at about 200 rpm). With stirring, 25 wt % of drinking water is added to the quantity of plaster, and stirring is continued until the material is creamy and spreadable (stirring time: at least 60 seconds at about 1000-1300 rpm).

The mixture is poured into circular PVC rings (diameter: 8 cm, height: 2 cm) which lie on a plate spread with filter paper. Any air bubbles produced are removed using a wooden spatula. A uniform surface is obtained by smoothing with a spatula, using gentle back-and-forth movements.

The test specimens are dried at room temperature for 24 hours, then taken from the rings and stored under standard conditions (23° C./50% humidity) for 7 days. Prior to the water storage, the dry weight of the test specimens is determined. To determine the water absorption based on DIN 18180, the samples are placed in drinking water so that they are covered by 5 cm of water. The samples must lie in such a way that water is able to reach the underside as well. After 1 hour, 2 hours, 3 hours, 6 hours, and 24 hours, the samples are removed, freed from water clinging to the surface, weighed, and then placed back in the water. After 24 hours the water storage is ended.

The relative water absorption is calculated using the following equation:

$$WA = \frac{m_2 - m_1}{m_1} * 100\%$$

$m_1$: weight of the test specimen before water storage $m_2$: weight of the test specimen after water storage Results In each of the tables the results of 24 h water storage of the test specimens with the mixed siliconates of the invention are contrasted with that of equimolar mixtures of the pure siliconates.

TABLE 1

| No. | Siliconate powder A | Addition in wt % | Siliconate powder B | Addition in wt % | Water absorption after 24 h in wt % |
|---|---|---|---|---|---|
| A0* | — | — | — | — | 13.60 |
| A1 | (1) Isobutyl:methyl:K = 0.5:0.5:1 | 0.2 | — | — | 2.34 |
| A2* | (C1a) Isobutyl:K = 1:1 | 0.2 | — | — | 2.56 |
| A3* | (C1a) Isobutyl:K = 1:1 | 0.11 | (C1b) Methyl:K = 1:1 | 0.09 | 7.86 |
| A4 | (4) Isobutyl:Methyl:K = 0.7:0.3:1 | 0.2 | — | — | 1.99 |
| A5* | (C1b) Methyl:K = 1:1 | 0.2 | — | — | 16.20 |

*not inventive

This experimental series shows that the mixed methyl/isobutylsiliconate of the invention in A1 is superior both to the pure isobutylsiliconate (A2) and to the corresponding mixture of isobutyl- and methylsiliconate (A3) and also to the pure methylsiliconate (A5) in terms of the water repellency effect. Furthermore, when comparing A1, A2 and A4, it can be seen that there is an optimum ratio of methyl/isobutyl.

TABLE 2

| No. | Siliconate powder A | Addition in wt % | Siliconate powder B | Addition in wt % | Water absorption after 24 h in wt % |
|---|---|---|---|---|---|
| B0* | — | — | — | — | 13.60 |
| B1 | (2) Isohexyl:methyl:K = 0.5:0.5:1 | 0.2 | — | — | 3.35 |
| B2* | (C2) Isohexyl:K = 1:1 | 0.2 | — | — | 4.98 |
| B3* | (C2) Isohexyl:K = 1:1 | 0.12 | (C1b) Methyl:K = 1:1 | 0.08 | 10.22 |

*not inventive

This experimental series likewise shows that the mixed methyl/isohexylsiliconate of the invention in B1 is superior both to the pure isohexylsiliconate (B2) and to the corresponding mixture of isohexyl— and methylsiliconate (B3) in terms of the water repellency effect.

TABLE 3

| No. | Siliconate powder A | Addition in wt % | Siliconate powder B | Addition in wt % | Water absorption after 24 h in wt % |
|---|---|---|---|---|---|
| C0* | — | — | — | — | 13.60 |
| C1 | (3) Isobutyl:methyl:K = 0.25:0.75:0.85 | 0.2 | — | — | 3.83 |
| C2* | (C3a) Isooctyl:K = 1:0.85 | 0.07 | (C3b) Methyl:K = 1:0.85 | 0.13 | 15.00 |
| C3 | (3) Isooctyl:Methyl:K = 0.25:0.75:0.85 | 0.3 | — | — | 2.61 |
| C4* | (C3a) Isooctyl:K = 1:0.85 | 0.11 | (C3b) Methyl:K = 1:0.85 | 0.19 | 15.00 |

*not inventive

This experimental series likewise shows that the mixed methyl/isooctylsiliconate of the invention in C1 and C3 is superior to the corresponding mixture of isooctyl- and methylsiliconate (C2 and C4) in terms of the water repellency effect.

USE EXAMPLES WITH GYPSUM PLASTERS

In the use examples G1-G4, typical commercial plasters in powder form (Goldband light finishing plaster and machine-application plaster MP 75 from Knauf Gips KG, Iphofen, Germany) are mixed effectively with varying amounts of potassium organosiliconate powder in dry form. This dry mix is then added in portions and with stirring to the mixing water, in accordance with the recipe indicated on the gypsum packaging, and, in accordance with DIN EN 196-1, the water and mix are stirred together using an electrically operated paddle stirrer at moderate speed, to form a homogeneous slurry (Goldband light finishing plaster: 300 g plaster powder and 200 g water; machine-application plaster MP 75: 300 g plaster powder and 180 g water—in each case as per pack instructions). The resulting slurry is then poured into PVC rings (diameter: 80 mm, height: 20 mm) and the plaster is cured at 23° C. and 50% relative humidity over 24 hours. After the demolding of the plaster specimens from the rings, they are dried to constant weight in a forced-air drying cabinet at 40° C. For the determination of the water absorption in accordance with DIN EN 520, the specimens, following determination of the dry weight, are stored under water for 120 minutes, with the samples placed horizontally on metal grids and the water level above the highest point of the specimens being 5 mm. After 120 minutes, the specimens are taken from the water, and allowed to drip off on a water-saturated sponge, and the percentage water absorption is calculated from the wet weight and the dry weight in accordance with the following formula:

percentage water absorption={[mass(wet)−mass(dry)]/mass(dry)}·100%.

Use Example G1

Water Repellency Treatment of Two Gypsum Plasters with a Potassium Organosiliconate Powder with a Molar Ratio of Isobutyl to Methyl Radical of 0.25:0.75 and with a Molar Ratio of Alkali Metal to Silicon of 0.85 (Product from Preparation Example 5)

Table 4 shows that a potassium organosiliconate powder with a comparatively small fraction of isobutyl groups and a molar ratio of alkali metal to silicon of 0.85 very efficiently imparts water repellency to gypsum plasters. Water absorption is well below 5% for both plasters at all levels of addition.

Use Example G2

Water Repellency Treatment of Two Gypsum Plasters with a Potassium Organosiliconate Powder with a Molar Ratio of Isobutyl to Methyl Radical of 0.70:0.30 and with a Molar Ratio of Alkali Metal to Silicon of 1.00 (Product from Preparation Example 4)

If the fraction of butyl groups is increased in comparison to use example 1, this increase has no effect on the water absorptions measured; the values in table 4 are close to the values for use example G1. Water absorption is well below 5% in both cases, at all levels of addition.

Use Example G3

Water Repellency Treatment of Two Gypsum Plasters with a Potassium Isobutylsiliconate Powder with a Molar Ratio of Alkali Metal to Silicon of 1.00 (Product from Preparation Example C1a)

If, in comparison to use example G2, a purely isobutyl-substituted potassium organosiliconate powder is used, then for both plasters, even with a molar ratio of alkali metal to silicon of 1.00, the water absorptions measured rise significantly.

Use Example G4

Water Repellency Treatment of Two Gypsum Plasters with a Potassium Organosiliconate Powder with a Molar Ratio of Isohexyl to Methyl Radical of 0.50:0.50 and with a Molar Ratio of Alkali Metal to Silicon of 1.00 (Product from Preparation Example 2)

Table 4 shows that a potassium organosiliconate powder with a fraction of 50% of isohexyl groups and a molar ratio of alkali metal to silicon of 1.00 efficiently imparts water repellency to gypsum plasters.

Use Example G5

Water Repellency Treatment of Two Gypsum Plasters with a Potassium Isohexylsiliconate Powder with a Molar Ratio of Alkali Metal to Silicon of 1.00 (Product from Preparation Example C2)

If, in comparison to use example G4, a purely isohexyl-substituted potassium organosiliconate powder is used, then for both plasters, even with a molar ratio of alkali metal to silicon of 1.00, the water absorptions measured are situated in the region of the untreated comparative value. Water absorption of 5% is not achieved by either of the plasters, at any levels of addition.

Use Example G6

Water Repellency Treatment of Two Gypsum Plasters with a Potassium Methylsiliconate Powder with a Molar Ratio of Alkali Metal to Silicon of 0.85 (Product from Preparation Example C1c)

Table 4 shows that a pure potassium methylsiliconate powder, in contrast to the corresponding mixed system (with isobutyl and methyl; see use example G1), brings about less efficient water repellency treatment of gypsum plasters.

in a first step, hydrolyzing organosilanes of the formula 1

$$(R^1)_a Si(Y)_b (-Si(R^2)_{3-c}(Y)_c)_d \quad (1)$$

or their hydrolysis/condensation products, or the organosilanes of the formula 1 together with their hydrolysis/condensation products, where $R^1$ and $R^2$ are each a monovalent, Si—C-bonded $C_{1-30}$ hydrocarbon radical which is unsubstituted or is substituted by halogen atoms, amino groups, thiol groups or $C_{1-6}$ alkyl- or $C_{1-6}$ alkoxy-substituted silyl groups, in which one or more nonadjacent —$CH_2$— units are optionally replaced by groups —O—, —S—, or —$NR^3$—, and in which one or more nonadjacent =CH— units are optionally replaced by groups —N=, $R^3$ is hydrogen or a monovalent $C_{1-8}$ hydrocarbon radical which is unsubstituted or substituted by halogen atoms or $NH_2$ groups, Y is H, F, Cl, Br, or $OR^4$, $R^4$ is a monovalent $C_{1-10}$ hydrocarbon radical which is unsubstituted or substituted by halogen atoms or silyl groups, in which one or more nonadjacent $CH_2$ units are optionally replaced by groups —O—, —S—, or —$NR^3$—, and in which one or more nonadjacent =CH— units are optionally replaced by groups —N=, a is 1, 2 or 3, and b, c, and d are 0, 1, 2 or 3, with the proviso that b+c≥1 and a+b+d=4, in the presence of water and basic salt of alkali metal cations, the amount of basic salt being calculated such that per mole of silicon there is 0.5 mol to 3 mol of cations, and, if the organosilanes of the formula 1 contain F, Cl, and/or Br radicals, a further mole of basic salt is present per mole of F, Cl, and Br, and in a second step, removing liberated compound(s) HY, in the form of gas, in a third step, removing water present in the mixture, and in a fourth step, isolating the salt in the form of a solid,

TABLE 4

Water absorption of gypsum specimens; method based on DIN EN 520

| Level addition (wt % based on dry gypsum solids) | G1 Knauf MP 75 | G1 Knauf Gold-band | G2 Knauf MP 75 | G2 Knauf Gold-band | G3* Knauf MP 75 | G3* Knauf Gold-band | G4 Knauf MP 75 | G4 Knauf Gold-band | G5* Knauf MP 75 | G5* Knauf Gold-band | G6* Knauf MP 75 | G6* Knauf Gold-band |
|---|---|---|---|---|---|---|---|---|---|---|---|---|
| 0 | 39.9 | 36.3 | 39.9 | 36.3 | 39.9 | 36.3 | 39.9 | 36.3 | 39.9 | 36.3 | 39.9 | 36.3 |
| 0.2 | 1.46 | 1.05 | 1.27 | 0.99 | 2.54 | 1.38 | 4.93 | 12.01 | 41.78 | 43.44 | 10.2 | 31.5 |
| 0.4 | 0.94 | 1.01 | 1.16 | 1.51 | 2.68 | 3.21 | 2.70 | 2.38 | 40.21 | 38.38 | 3.4 | 2.3 |
| 0.6 | 0.84 | 1.14 | 2.68 | 1.78 | 3.52 | 3.22 | 2.49 | 2.18 | 38.89 | 37.94 | 2.0 | 1.2 |

*not inventive

The invention claimed is:

1. Solid salts of organo radical-containing organosilanols, of their hydrolysis/condensation products, or of organo radical-containing organosilanols together with their hydrolysis/condensation products, with alkali metal cations, wherein the molar ratio of cation to silicon is 0.5 to 3, wherein at least 1 mol % and not more than 99 mol % of the organo radicals are selected from the group consisting of methyl and ethyl radicals and mixtures thereof, and organo radicals other than methyl and ethyl radicals contain at least 4 C atoms, produced by a process, comprising:

wherein at least 1% and not more than 99% of the radicals $R^1$ and $R^2$ are methyl and/or ethyl radicals and radicals $R^1$ and $R^2$ which are not methyl or ethyl radicals contain at least 4 C atoms.

2. The solid salts of claim 1, in which 10% to 90% of all organic radicals are methyl radicals and/or ethyl radicals.

3. The solid salts of claim 1, in which all organic radicals are hydrocarbon radicals having 1 to 8 carbon atoms.

4. A hydrophobizing composition, comprising a solid salt of claim 1.

5. A process for hydrophobing a mineral substance, building material, or fibrous substance, comprising adding a solid salt of claim 1.

6. A building material in powder form, comprising a solid salt of claim 1.

* * * * *